United States Patent [19]

Gunther

[11] 4,282,179

[45] Aug. 4, 1981

[54] DISINFECTION WITH ISOPROPANOL VAPOR

[75] Inventor: Donald A. Gunther, Erie, Pa.

[73] Assignee: American Sterilizer Company, Erie, Pa.

[21] Appl. No.: 119,788

[22] Filed: Feb. 8, 1980

[51] Int. Cl.³ ............................ A61L 2/06; A61L 2/20
[52] U.S. Cl. ........................................ 422/27; 422/28; 422/33; 424/343; 424/248.4
[58] Field of Search .................... 422/27, 28, 29, 31, 422/33; 424/343, 248.4

[56] References Cited

U.S. PATENT DOCUMENTS

| 246,494 | 8/1881 | Gibson | 422/27 X |
|---|---|---|---|
| 867,831 | 10/1907 | Nathan | 422/29 |
| 903,853 | 11/1908 | Gartner | 422/27 |
| 2,832,664 | 4/1958 | Bloch | 422/28 |
| 3,457,031 | 7/1969 | Linder et al. | 422/33 X |
| 3,468,885 | 9/1969 | Sanne et al. | 424/248.4 X |
| 3,481,689 | 12/1969 | Rosdahl et al. | 422/28 |
| 3,908,031 | 9/1975 | Wistreich et al. | 422/27 X |
| 3,963,438 | 6/1976 | Banez | 422/33 X |
| 3,992,147 | 11/1976 | Christian et al. | 422/32 |

FOREIGN PATENT DOCUMENTS

| 2445110 | 4/1976 | Fed. Rep. of Germany | 422/28 |
|---|---|---|---|
| 2540263 | 3/1977 | Fed. Rep. of Germany | 422/28 |

*Primary Examiner*—Barry Richman
*Attorney, Agent, or Firm*—Robert D. Yeager

[57] ABSTRACT

A low temperature method for the cleaning and disinfection of heat- and liquid-sensitive articles that are brought into physical contact with patients during diagnostic evaluation, surgery or therapy. These articles, such as endoscopes, bronchoscopes and related equipment are thus subject to contamination by microorganic pathogens and consequently may serve as transmittal agents for noscomial infection. In the method of this invention, quick, penetrating and adequate disinfection can be obtained by the use of a vapor consisting essentially of from 40 to 100% isopropanol and the remainder consisting predominantly of water vapor. The aforesaid articles are brought into direct contact and totally enveloping contact with the vapor at a temperature between 45° C. and 65° C. for a period effective to destroy the pathogens.

When the articles are then removed from vapor contact, any condensed isopropanol on the surfaces of the article quickly evaporates. This method can be operated in a disinfection chamber at constant atmospheric pressure or a vacuum can be drawn prior to introduction of the vapor into the chamber. Disinfection generally results in from ½ hour to 1½ hours, with shorter times possible in the vacuum cycle.

6 Claims, No Drawings

DISINFECTION WITH ISOPROPANOL VAPOR

BACKGROUND OF THE INVENTION

1. Field of the Invention

This invention relates to the disinfection of medical apparatus; more particularly to the disinfection of heat- and liquid-sensitive medical apparatus by the use of isopropanol in the vapor phase.

2. Description of the Prior Art

Conventional hospital sterilization practices call for the use of steam or ethylene oxide gas. There are limitations, however, on the types of equipment that may be subjected to these sterilants. Steam may cause damage to heat-sensitive materials such as plastics, rubber and the like. Ethylene oxide gas sterilization, while carried out at lower temperatures than steam sterilization, generally requires a relatively long aeration period or "turn-around time". Certain types of medical apparatus, especially expensive items, cannot be out of service for that period of time. As to this latter apparatus, when steam sterilization is also prohibited because of material limitations, the hospital generally resorts to the manual application of liquid disinfectants. Even this procedure has serious drawbacks, however, because parts of an instrument being disinfected in such manner may be subject to chemical attack and/or other degradation by the liquid disinfectant, especially when immersion is used as the application technique.

Specific types of medical apparatus that are not subject to steam and/or ethylene oxide gas sterilization for the reasons mentioned above include endoscopes, respiratory therapy equipment and anesthesia equipment, wrapped or unwrapped.

Endoscopes are instruments for the visual examination of body cavities, such as bronchoscopes, laparoscopes, arthoscopes, and upper and lower GI endoscopes. Fiberscopes or flexible fiberoptic endoscopes are those endoscopes having fiberoptic lighting; these are particularly adapted to bending and generally provide a brighter light than standard endoscopes. Endoscopic accessory or related equipment includes cytology brushes and biopsy forceps used in gastrointestinal endoscopy. The need for efficient and effective disinfection and cleaning of endoscopic equipment has been highlighted due to infections related to use of this kind of equipment in hospitals. Nosocomial (hospital-acquired) infections have been specifically associated with inadequately cleaned respiratory equipment.

The Ad Hoc Committee of Infection Control in the Handling of Endoscopic Equipment, coordinated by the Association of Practitioners in Infection Control (APIC), in January 1978 established the following guidelines for the cleaning and disinfection of flexible fiberoptic endoscopes used in gastrointestinal endoscopy:

"1. Scrupulous mechanical cleaning of insertion tube and channels, using a detergent, is imperative. This must be done immediately after use to prevent the drying of secretions.

2. Inspection of equipment for damage.

3. Disinfection of endoscopic insertion tube and all channels, performed with a chemical substance having disinfecting action sufficient to kill all microorganisms (gram-positive and gram negative bacteria, fungi mycobacteria, and lipophilic and hydrophilic viruses) except bacterial spores when used according to manufacturer's instructions.

4. Adequate rinsing must follow such disinfection.

It should be emphasized that adequate rinsing is necessary to prevent possible residual toxic effects of the disinfectant chemical and/or detergent. The risks of toxicity with regard to particular disinfectants and/or detergents need further exploration.

5. The insertion tube and inner channels should be thoroughly and immediately air dried after cleaning and prior to storage. (Bacteria will multiply in a moist environment).

6. Instruments to be stored.

7. Ethylene oxide sterilization is not generally practical. If used, it is imperative that meticulous cleaning be accomplished as described in Guideline 1, and that it be followed by adequate aeration.

8. Because of the spring-like structural configuration, accessories such as biopsy forceps and cytology brushes have been shown to be extremely difficult to clean and disinfect. After immediate surface cleaning with a detergent/disinfectant, and rinsing, it is advisable to use either steam under pressure or gas (ethylene oxide sterilization) or any other treatment which has the capability of penetrating the spring-like structures.

It is emphasized that the heat treatments described be applied only to accessories such as biopsy forceps, not to fiberoptic devices. Improved structural configurations of the accessories and/or more efficient cleaning methods need further exploration."

These guidelines illustrate some of the special considerations and problems in disinfecting flexible fiberoptic endoscopes (fiberscopes). Liquid disinfectants, detergents, distilled water, steam and ethylene oxide gas (when possible), have thus been used in varying combinations to accomplish disinfection of this type of equipment. Even when disinfection has been adequate, time-consuming air drying is required and instruments are not immediately available for re-use. Presently, endoscopic equipment is either simply cleaned before re-use or is disinfected by immersion in some liquid biocidal agent. Simple cleaning is not an adequate process to protect against cross infection. While disinfecting by immersion in a liquid agent can be effective, it does not permit packaging of the item to protect it from recontamination, in handling, transit or storage. Furthermore, it often damages the device, and generally requires copious rinsing with sterile distilled water to remove the residual agent before use. Additionally, immersion and rinsing are at the discretion of the worker and are frequently inadequate. Liquids also exert a dissolving action on certain polyvinyl chlorides, silicones, acrylics, resins, lens cements and other materials of the endoscopes. Detergents can be abrasive and corrosive. The cumulative effects diminish the use-life of the equipment.

An optimum cleaning and disinfection process for endoscopes, including fiberoptic endoscopes and related equipment, would therefore incorporate the following features:

1. Operate at low temperatures
2. Operate at atmospheric pressure or below (vacuum)
3. Leave no residual chemical
4. Provide moisture-free articles following disinfection
5. Require no aeration time 6. Provide adequate penetration of springs and interstices by disinfectant 7. Provide adequate bactericidal action.

One object of this invention, therefore, is to provide a quick, penetrating, low-temperature treatment of articles at atmospheric pressure or below (vacuum) which destroys infectious organisms, yields essentially moisture-free articles without aeration time, and leaves no residual agent.

Another objective is to provide an efficient and uniform treatment for all endoscopic (including fiberoptic) and accessory equipment, as well as for other articles which cannot because of their structure or the materials of which they consist be sterilized by conventional methods, or cannot be disinfected by immersion.

Nathan U.S. Pat. No. 867,831 discloses the use of alcohol fumes to sterilize beer vessels. The vapors condense within a pressurized chamber during sterilization. The condensate will also dissolve resins formed in the beer-manufacturing process. These high pressure, moisture and resin-dissolving features, which are favorable to beer vessels, would damage endoscopic equipment.

Gibson U.S. Pat. No. 246,494 uses alcohol vapors and steam to restore feathers. This is also a high temperature, pressure process contraindicated for endoscopes.

Gartner U.S. Pat. No. 903,853 teaches the use of a methyl alcohol in approximately 55% concentration or ethyl alcohol and water vapor in large quantities. The sterilization cycle comprises essentially the following steps: (1) exhaustion of a sterilization chamber to a pressure-gauge vacuum of 700 mm; (2) introducing a mixture of water and methyl alcohol into the chamber and vaporizing the same; (3) a timed exposure (e.g., about 20 minutes) after vaporization is completed; (4) admission of air to atmospheric pressure; (5) all valved access to the chamber is closed and temperature is maintained constant for 1½ hours from initiation of treatment; and, finally (6) a half-hour sweep of a strong current of air through the chamber. The articles are preferably subjected to pressure after completion of this complicated cycle. The teaching emphasizes the importance of large vapor quantity and exhausting the chamber of air to a high degree before introducing the disinfectant in order to accomplish disinfection. Thus biocidal activity is dependent on large quantities of alcohol and water vapors operating under a high vacuum. At 55% concentration, vapor biocidal activity without this extremely high exhaustion would be inadequate for disinfection. The large vapor quantities required would also penetrate and exert harmful dissolving action on synthetic endoscopic materials.

Thus the alcohols and methods of these patents are unsuitable for disinfection of endoscopic equipment in modern hospital practice.

SUMMARY OF THE INVENTION

A process that is suitable for the disinfection of such heat-sensitive and liquid-sensitive hospital equipment has now been found to comprise the topical employment of vaporized isopropanol usually in admixture with water vapor in preferably minor proportion. The term "heat-sensitive" as used herein refers to materials or articles which cannot be exposed to a temperature greater than 150° F. (65.56° C.). "Liquid-sensitive" as used herein refers to those materials or articles which are adversely affected by contact with liquids. The process of the present invention may be applied to any medical item or device that heretofore could not be sterilized at all; items which could not be sterilized routinely after each use; or those which need not be sterilized but only disinfected.

A process that is suitable for the disinfection of such heat- and liquid-sensitive hospital equipment has now been found to consist in the topical employment of vaporized isopropanol usually in admixture with water vapor in preferably minor proportion. While isopropanol has been known as a strong liquid disinfectant, its solubility in water permitting its easy dilution, its high molecular density in liquid phase and its resultant propensity to attack components of the aforesaid heat- and liquid-sensitive hospital equipment such as endoscopes had limited its usefulness for such disinfection. Thus, even though isopropanol in the liquid phase is known as a disinfectant (see for example U.S. Pat. Nos. 2,832,664 and 3,992,147) for the liquid sterilization of surgical catgut and seed husks, it was found to be incompatible with such sensitive articles of hospital equipment as endoscopes. For example, when the synthetic (i.e. plastic or elastomeric) materials of the endoscopic instruments are placed in the high density liquid environment, liquid isopropanol or other alcohol will be absorbed into the plastic indefinitely until the plastic is saturated with the liquid, resulting in damage to the material. The plastic (synthetic resin) is dissolved by the action of the liquid alcohol, and components and additives of the resin (silicone, polyvinyl chlorides, resins, cements, acrylics, polycarbonates, etc.) are leached into solution.

On the other hand, isopropanol vapor will not leach these materials. The maximum effects would be swelling from absorption of the vapor with subsequent recovery when removed from that environment.

The process of the invention comprises as a first step generating isopropanol vapor from a solution of isopropanol and water. Small volume percentages of butanol and morpholine also may be added to the solution. The concentration of isopropanol may range from 40 to 100% isopropanol, with an optimum concentration of 70%. The vapor is generated at a temperature in the range of 45° C. to 65° C., a preferred temperature being about 55° C., that is, sufficiently high to produce a significant vapor pressure, but below boiling point so that equilibrium is reached. The vapor is introduced into a chamber in which the articles to be disinfected are placed. The cycle may be run at atmospheric pressure or a vacuum (from about 25 to 35 mm. mercury absolute) may be drawn in the chamber prior to introduction of the vapor. Articles are exposed to the isopropanol vapor until disinfection is achieved. This may be in 4 minutes, and does not exceed two hours. At the end of the cycles, the vapor is exhausted from the chamber. There is no need for aeration; vaporization will flash off any condensed isopropanol. There is generally no residual agent; if any possible agent remains it would be negligible in amount or effect.

DESCRIPTION OF THE PREFERRED EMBODIMENTS

Optimal conditions for isopropanol vapor phase disinfection are 70% by volume isopropanol and 30% by volume water at 55° C. The effective temperature range for the process is based on a maximum temperature, about 65° C. (determined by the heat resistance of the article) and a minimum temperature, about 45° C., below which impractically long exposure times are required. The temperature of 55° C. (131° F.) was selected because virtually all synthetic (plastic/elastomeric) materials commonly used in endoscopic equipment are stable and unaffected by that temperature. The 70% by volume isopropanol/ 30% by volume water mixture is selected because this is the mixture most readily available. Higher concentrations will follow chemical and biocidal kinetics with a modest increase in activity up to 100% by volume isopropanol and a rapid decrease in activity occurring at less than 40% by volume isopropanol in 60% by volume water. Small volume percentages of butanol (e.g., up to about 6%) and/or morpholine (e.g., up to about 5%) when added to the isopropanol/water mixture tend to increase the biocidal activity of the vapor.

EXAMPLE

Tests were conducted under the just-described conditions by placing an amount of the isopropanol/water mixture in a sterilization chamber substantially in excess of that needed in order to ensure vapor phase saturation.

The organisms used in the tests were *Pseudomonas aeruginosa* and *Staphlococcus aureus*. Glass plates and penicylinder carriers were innoculated from a broth culture to a population of $10^8$ organisms per carrier, which provided a condition of high population of resistant organisms protected by much organic debris. Penicylinder carriers are standard challenge detectors, used in hospital sterilization "packs" (packages of wet or dry, hard or soft goods or articles to be sterilized) to determine the bacteria kill achieved in a cycle. Penicylinders are a testing requirement to satisfy the EPA relative to the effectiveness of a disinfecting agent.

Plate carriers were exposed in uncovered petri dishes. Isopropanol vapor phase disinfection was then carried out in an atmospheric cycle. The isopropanol-water mixture was vaporized into a closed chamber, at atmospheric pressure, for 16 minutes.

Other plate carriers of the same organism populations were again exposed under the same conditions of temperature and concentration. This time, the vapor phase disinfection was run in a vacuum cycle for 16 minutes. A vacuum of approximately 28 inches of mercury was drawn in the closed chamber and then the isopropanol-water mixture was vaporized into the chamber and pressure restored to atmospheric. After exposure, each carrier was cultured separately to determine if all the carrier organisms were killed. Table A gives the results of these experiments as a function of exposure time, and also indicates the comparative effectiveness of the atmospheric pressure cycle and the vacuum cycle.

TABLE A $10^8$ ORGANISMS ON GLASS PLATE:
55 C. 70% v/v ISOPROPANOL, 30% v/v WATER

| | VACUUM CYCLE | |
|---|---|---|
| | Organisms Surviving | |
| Time | P. Aeruginosa | S. Aureus |
| 8 Minutes | 0 | TNTC* |
| 16 Minutes | 0 | $10^2$ |
| ATMOSPHERIC PRESSURE CYCLE | | |
| 4 Minutes | TNTC | TNTC |
| 16 Minutes | 0 | TNTC |

*Too numerous to count

The results shown in Table A indicated that *Pseudomonas aeruginosa* was the least resistant organism and it was therefore dropped from further tests. In the subsequent experiments reported below in Table B, only *Staphlococcus aureus* was innoculated in a $10^8$ population per penicylinder carrier, this micro-organism being especially suitable for testing inasmuch as it is the resistant pathogen commonly found to be the causative factor in nosocomial infections. Again, six carriers were exposed in an open petri dish and six were exposed sealed in a "peel pouch". A 70% by volume isopropanol and 30% by volume water mixture was placed in the chamber in an amount in excess of that calculated to ensure vapor phase saturation. The mixture was vaporized in the chamber at a temperature of 55° C. The experiment was run in a substantially atmospheric pressure cycle, and then duplicated in the vacuum cycle. Table B shows the results, again as a function of time, with a comparison of atmospheric pressure and vacuum cycles:

TABLE B

*S. AUREUS*, $10^8$/CARRIER
55 C. 70% v/v ISOPROPANOL/30% v/v WATER

| | VACUUM CYCLE | |
|---|---|---|
| Time | Bare | Pouch |
| 16 Minutes | 5 of 6 Positive Growth | 6 of 6 Positive Growth |
| 32 Minutes | 2 of 6 Positive Growth | 1 of 6 Positive Growth |
| 32 Minutes | All Negative Growth | All Negative Growth |
| 32 Minutes | All Negative Growth | All Negative Growth |
| 64 Minutes | All Negative Growth | All Negative Growth |
| 64 Minutes | All Negative Growth | All Negative Growth |
| 64 Minutes | All Negative Growth | All Negative Growth |
| 70 Minutes | All Negative Growth | All Negative Growth |
| ATMOSPHERIC PRESSURE CYCLE | | |
| Time | Bare | Pouch |
| 32 Minutes | 5 of 6 Positive Growth | 6 of 6 Positive Growth |
| 64 Minutes | 2 of 6 Positive Growth | 3 of 6 Positive Growth |
| 100 Minutes | 1 of 6 Positive Growth | All Negative Growth |
| 100 Minutes | 3 of 6 Positive Growth | 4 of 6 Positive Growth |
| 128 Minutes | 1 of 6 Positive Growth | All Negative Growth |
| 128 Minutes | 6 of 6 Positive Growth | 5 of 6 Positive Growth |
| 128 Minutes | 4 of 6 Positive Growth | 5 of 6 Positive Growth |
| 128 Minutes | All Negative Growth | All Negative Growth |
| 160 Minutes | All Negative Growth | All Negative Growth |
| 160 Minutes | All Negative Growth | All Negative Growth |

The above Tables thus indicate that adequate disinfection with a bacteriological kill greater than 50% can be obtained in from 64 to 100 minutes (1 to 2 hours); and complete sterilization in from 128 to 160 minutes (2–3 hours).

Utilizing the features of isopropanol vapor compatible with heat and liquid sensitive equipment such as endoscopes, as discussed above, and the disinfection/sterilization data of the test results, it is possible to achieve an effective disinfection cycle for this type of equipment by the use of isopropanol and water in the vapor phase.

What is claimed is:

1. A method of disinfecting heat-sensitive or liquid-sensitive articles that are brought into physical contact with patients in the course of examination, surgery or therapy and that consequently are subject to contamination with microorganic pathogens, the said method comprising:

bringing such article subsequent to exposure to any such contamination into direct, sustained and totally enveloping contact with a substantially liquid-free vapor at a pressure not substantially exceeding atmospheric pressure, said vapor consisting essentially of from 40% by volume to 100% by volume of isopropanol and the remainder consisting predominantly of water vapor;

maintaining said contact at a temperature between about 45° C. and 65° C. for a period effective to destroy said pathogens;

removing the said article from contact with the isopropanol-containing vapor; and allowing any condensed isopropanol on the surface of the so-treated article to evaporate from the said surface.

2. The method of claim 1 wherein the concentration of isopropanol is about 70% by volume and the concentration of water vapor is about 30% by volume.

3. The method of claim 1 wherein the pressure of the disinfecting vapor is substantially atmospheric.

4. The method of claim 1 wherein there is a vacuum from 25 to 35 mm. mercury absolute drawn from the atmosphere surrounding such article prior to introduction of the isopropanol-containing vapor.

5. The method of claim 1 wherein the temperature of the disinfecting vapor is about 55° C.

6. The method of claim 1 wherein the disinfecting vapor is at a subatmospheric pressure.

* * * * *

UNITED STATES PATENT AND TRADEMARK OFFICE
CERTIFICATE OF CORRECTION

PATENT NO. : 4,282,179

DATED : August 4, 1981

INVENTOR(S) : Donald A. Gunther

It is certified that error appears in the above-identified patent and that said Letters Patent are hereby corrected as shown below:

Col. 1, line 53, delete "of" and substitute therefor --for--; and

Col. 3, line 4, delete "object" and substitute therefor --objective--.

Signed and Sealed this

Third Day of November 1981

[SEAL]

Attest:

Attesting Officer

GERALD J. MOSSINGHOFF

Commissioner of Patents and Trademarks